United States Patent [19]

Bewert et al.

[11] Patent Number: 4,701,546
[45] Date of Patent: Oct. 20, 1987

[54] PREPARATION OF 2-(N-FORMYLAMINO)-PROPIONITRILE

[75] Inventors: Wolfgang Bewert, Frankenthal; Hans Kiefer, Wachenheim, both of Fed. Rep. of Germany

[73] Assignee: BASF Aktiengesellschaft, Ludwigshafen, Fed. Rep. of Germany

[21] Appl. No.: 866,775

[22] Filed: May 23, 1986

[30] Foreign Application Priority Data

Jun. 12, 1985 [DE] Fed. Rep. of Germany ....... 3520982

[51] Int. Cl.$^4$ .......................................... C07C 121/43
[52] U.S. Cl. ................................................. 558/445
[58] Field of Search ........................................ 558/445

[56] References Cited

U.S. PATENT DOCUMENTS

| 2,461,842 | 2/1949 | Olin | 558/445 |
| 3,017,425 | 1/1962 | Bortnick | 558/445 |

FOREIGN PATENT DOCUMENTS

| 734725 | 3/1943 | Fed. Rep. of Germany . | |
| 735771 | 6/1943 | Fed. Rep. of Germany | 558/445 |
| 976959 | 3/1951 | France | 558/445 |

OTHER PUBLICATIONS

Cyanamid, "The Chemistry of Acrylonitrile", 2nd ed., (1959); Published by American Cyanamid Co., pp. 24 and 197.
Organic Reactions, vol. 5, Chapter#2, "Cyanoethylation", by Bruson (1949), pp. 87, 88, 89, 120.
Bull. Soc. Chim. France 1957, pp. 1108-1110; Mastagli et al.
Houben-Weyl, Methoden der Organischen Chemie, (1957) vol. XI/1, pp. 272-273, and (1958) vol. XI/2, pp. 496-497.

*Primary Examiner*—Joseph Paul Brust
*Attorney, Agent, or Firm*—John H. Shurtleff

[57] ABSTRACT 2-(N-Formylamino)-propionitrile is prepared by reacting acrylonitrile with formamide in the presence of a basic compound by a process in which the basic compound used is a tertiary nitrogen base.

15 Claims, No Drawings

PREPARATION OF 2-(N-FORMYLAMINO)-PROPIONITRILE

The present invention relates to an improved process for the preparation of 2-(N-formylamino)-propionitrile by reacting acrylonitrile with formamide in the presence of a basic compound:

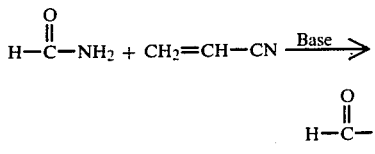

German Pat. No. 734,725 discloses that alkali metal bases, such as sodium hydroxide and sodium, can be used as basic catalysts in this reaction, although the achievable yields of 48–55% are unsatisfactory, as our own experiments have shown. In the process described in Bull. Soc. Chim. France 1957, page 1108, the reaction is carried out in the presence of a basic ion exchanger containing quaternary ammonium groups, but this procedure gives relatively large amounts of bis-(2-N-formylimino)-propionitrile as an undesirable by-product.

It is also known that 2-aminopropionitrile can be prepared by cyanoethylation of ammonia (Houben-Weyl, Methoden der organischen Chemie, volume XI/1, page 272, and volume XI/2, page 496), so that the title compound can also be obtained in this manner by formylation of this compound. However, this method has the serious disadvantage that the bis- and triscyanoethylamines too are always obtained as by-products.

It is an object of the present invention to make it possible to obtain 2-(N-formylamino)-propionitrile in a more economical manner than in the past.

We have found that this object is achieved by an improved process for the preparation of 2-(N-formylamino)-propionitrile by reacting acrylonitrile with formamide in the presence of a basic compound, wherein the basic compound used is a tertiary nitrogen base.

Particularly useful tertiary nitrogen bases are those having a $p_K$ of less than 5, for example aliphatic teritary amines, such as trimethylamine ($p_K=4.26$), triethylamine ($p_K=3.13$), tripropylamine ($p_K=3.35$), tributylamine ($p_K=3.11$), dimethyldodecylamine and N,N,N',N'-tetramethyl-1,3-diaminopropane, heterocyclic-aliphatic tertiary amines, such as N-methylpiperidine and N,N'-dimethylpiperazine, and bicyclic tertiary amines, such as 1,4-diazabicyclo[2.2.2]-octane (DABCO, $p_K=2.95$).

The amount of catalytic nitrogen base is not critical since it merely affects the reaction rate. In general, the amount of this substance necessary to achieve a sufficiently rapid conversion is from 1 to 50 mol % per mole of acrylonitrile.

Formamide and acrylonitrile react with one another in stoichiometric amounts, but it is advantageous to use the formamide in up to about a 20-fold molar excess, based on the acrylonitrile. The preferred molar ratio is from 2:1 to 10:1.

In order, where possible, to suppress the polymerization of the acrylonitrile, it is advisable additionally to use a polymerization inhibitor, such as hydroquinone, hydroquinone monomethyl ether, 3-tert-butyl-4-hydroxyanisole, 2,6-di-tert-butyl-4-methylphenol or a gallate, in a concentration of about 0.001–0.5% by weight, based on the acrylonitrile.

The presence of a solvent is not generally required but may be advantageous particularly when the reactants are not sufficiently soluble in one another.

Examples of suitable solvents are polar solvents such as dimethylformamide, dimethylacetamide, N-methylpyrrolidone, tetrabutylurea, dioxane and tetrahydrofuran.

For reasons relating to process engineering, the procedure is preferably carried out under atmospheric pressure, although it is also possible to employ slightly elevated pressure, eg. up to 5 bar, for example when a very readily volatile tertiary amine or a readily volatile solvent is used.

If the reaction is carried out by a batchwise procedure, the formamide, the nitrogen base and, if required, the solvent are advantageously initially taken, and the acrylonitrile or a solution of the latter is gradually added. The continuous procedure is carried out in a similar manner, the formamide and the nitrogen base on the one hand and the acrylonitrile on the other being combined in a roughly constant molar ratio.

In other respects, the novel process does not exhibit any special features in terms of process engineering, so that further description is unnecessary. The same applies to the procedure for working up the reaction mixture.

2-(N-Formylamino)-propionitrile is known to be an important intermediate for the synthesis of vitamin $B_1$ and furthermore opens up an advantageous route to the direct secondary product $\beta$-alanine, which is also important.

EXAMPLES 1 to 10

A solution of 450 g (10 moles) of formamide and a g (a' mole) of a tertiary nitrogen base was initially taken in each case, and 53 g (1 mole) of acrylonitrile stabilized with 40 ppm of hydroquinone monomethyl ether were added at $T_1°$ C. in the course of about 1 hour. The reaction mixture was then refluxed for a further 3 hours, the temperature increasing to $T_2°$ C. or being kept at $T_1$ ($T_2=T_1$).

Working up by a conventional distillation method gave 2-(N-formylamino)-propionitrile in a yield of y % (bp. 130° C/1 mbar), and the unconverted starting materials were recovered virtually quantitatively. The amount of by-products was about 0.5–3%, based on the acrylonitrile used.

Details of the experiments and the results of these are shown in the Table below.

| Example No. | Tertiary nitrogen base | a [g] | a' [mole] | $T_1$ [°C.] | $T_2$ [°C.] | y [%] |
|---|---|---|---|---|---|---|
| 1 | Triethylamine | 20 | 0.2 | 80 | 100 | 83 |
| 2 | Tri-n-propylamine | 20 | 0.14 | 130 | 130 | 81 |
| 3 | N,N,N',N'—Tetramethyl-1,3-diaminopropane | 3 | 0.02 | 130 | 130 | 76 |
| 4 | 1,4-Diazabicyclo[2.2.2]-octane | 12 | 0.09 | 130 | 130 | 76 |
| 5 | Tri-n-butylamine | 20 | 0.11 | 130 | 130 | 75 |
| 6 | Dimethylisopropylamine | 10 | 0.12 | 115 | 130 | 75 |
| 7 | 1,8-Diazabicyclo[5.4.0]-undec-7-ene | 10.5 | 0.07 | 130 | 130 | 72 |
| 8 | N,N,N',N',N"—Penta- | 3 | 0.017 | 120 | 130 | 75 |

-continued

| Example No. | Tertiary nitrogen base | a [g] | a' [mole] | $T_1$ [°C.] | $T_2$ [°C.] | y [%] |
|---|---|---|---|---|---|---|
| | methyldiethylene triamine | | | | | |
| 9 | N,N,N',N'—Tetramethyl-2,2'-diaminodiethyl ether | 20 | 0.13 | 120 | 130 | 73 |
| 10 | N—Methylpiperidine | 14 | 0.14 | 125 | 130 | 71 |

We claim:

1. A process for the production of 2-(N-formylamino)-propionitrile which comprises:
   reacting 1 mole of acrylonitrile with 2 to 20 moles of formamide at a temperature of from 80° C. to 130° C. and in the presence of a catalyst, said catalyst consisting essentially of a tertiary nitrogen amine base having a $p_K$ value of less than 5.

2. A process as claimed in claim 1 wherein the tertiary amine catalyst is used in an amount of 1 to 50 mole % per mole of the acrylonitrile.

3. A process as claimed in claim 1 wherein the molar ratio of formamide to acrylonitrile is from 2:1 to 10:1.

4. A process as claimed in claim 1 where in a polymerization inhibitor for the acrylonitrile is added in an amount of about 0.001 to 0.5% by weight, based on the acrylonitrile.

5. A process as claimed in claim 1 wherein the tertiary amine catalyst is triethylamine.

6. A process as claimed in claim 1 wherein the tertiary amine catalyst is tri-n-propylamine.

7. A process as claimed in claim 1 wherein the tertiary amine catalyst is N,N,N',N'-tetramethyl-1,3-diaminopropane.

8. A process as claimed in claim 1 wherein the tertiary amine catalyst is 1,4-diazabicyclo[2.2.2]-octane.

9. A process as claimed in claim 1 wherein the tertiary amine catalyst is tri-n-butylamine.

10. A process as claimed in claim 1 wherein the tertiary amine catalyst is dimethylisopropylamine.

11. A process as claimed in claim 1 wherein the tertiary amine catalyst is 1,8-Diazabicyclo[5.4.0]-undec-7-ene.

12. A process as claimed in claim 1 wherein the tertiary amine catalyst is N,N,N',N',N''-pentamethyl-diethylenetriamine.

13. A process as claimed in claim 1 wherein the tertiary amine catalyst is N,N,N',N'-tetramethyl-2,2'-diaminodiethyl ether.

14. A process as claimed in claim 1 wherein the tertiary amine catalyst is N-methylpiperidine.

15. A process as claimed in claim 1 wherein the tertiary amine catalyst is selected from the group consisting of trimethylamine, triethylamine, tripropylamine, tributylamine, dimethyldodecylamine, N,N,N',N'-tetramethyl-1,3-diaminopropane, N-methylpiperidine, N,N'-dimethylpiperazine and 1,4-diazabicyclo[2.2.2]-octane.

* * * * *